United States Patent [19]

Shakkottai et al.

[11] Patent Number: 4,915,816
[45] Date of Patent: Apr. 10, 1990

[54] POLYMER HYGROMETER FOR HARSH ENVIRONMENTS

[76] Inventors: Parthasarathy Shakkottai, 2622 Gardi St., Duarte, Calif. 91010; Daniel D. Lawson, 5542 Halifax Rd., Arcadia, Calif. 91006; Shakkottai P. Venkateshan, Gandhi Nagar, Adyar, Madras 600020, India

[21] Appl. No.: 240,736

[22] Filed: Sep. 6, 1988

[51] Int. Cl.[4] .......................................... G01N 27/46
[52] U.S. Cl. ..................................... 204/430; 73/335; 73/336.5; 204/153.1
[58] Field of Search ................ 204/1 W, 430; 73/335, 73/336.5

[56] References Cited

U.S. PATENT DOCUMENTS

| 4,083,765 | 4/1978 | Lawson | 204/195 W |
| 4,280,885 | 7/1981 | Savery | 204/430 |
| 4,514,278 | 4/1985 | Stephens et al. | 204/430 |
| 4,681,855 | 7/1987 | Huang | 436/39 |

OTHER PUBLICATIONS

Humidity—Temperature Transmitter, Rotronic Instrument Corp. Brochure, HT150 Series, 7 High St., Huntington, NY, 11743, 1988.
"Vaporsense 1000", Pacer Systems Inc. Brochure, 900 Technology Park Dr., Billerica, MA, 01821, 1988.
"Capacitive Solid State Dew Point Hygrometer", Honeywell Brochure, 12001 Highway 55, Plymouth, MN, 55441.
"ECON 200—The New Industrial Dew Point Measuring System", Vaisala Brochure, 2 Tower Office Park, Woburn, MA 01801.

Primary Examiner—T. Tung

[57] ABSTRACT

The polymer hygrometer with lithium doped Nafion was developed to meet the need for a reliable sensor for determining the relative humidity in harsh environments of pulp and paper mills. The sensor can operate in atmospheres that have organic vapors and dust, is unaffected by sulphur dioxide, acidic vapors and strong oxidizing agents. Exceptional stability is shown by the sensor which has withstood twelve months of continuous operation in a paper mill drier duct at temperatures near 65° C. and air flow velocity of 10 m/s with no degradation or calibration change. Materials used in construction of the sensor such as glass, silver filled epoxy, Teflon, platinum wire, and Nafion contribute to ruggedness and immunity to harsh environments.

4 Claims, 14 Drawing Sheets

POLYMER HYGROMETER FOR HARSH ENVIRONMENTS

This invention was made with Government support under contract No DE-AI05-84 CE40684 awarded by NASA. The Government has certain rights in this invention.

BACKGROUND OF THE INVENTION

1. Field of the Invention

The present invention relates to measuring moisture content in moist environments by using the a.c. conductivity of a strip of hygroscopic polymer Nafion. The conductivity is a function of humidity and temperature.

2. Description of Prior Art

A long-lasting electrolytic hygrometer capable of use in any moist gaseous environment, based on a measurement of d.c. current required to electrolyze water adsorbed by Nafion, was described by D. D. Lawson (ref. 1) in U.S. Pat. No. 4,083,765. The configuration of this sensor was tubular; moist air was drawn in through a Nafion tube and electrolyzed to a totally dry state. From the flow rate and current, humidity was calculated. This type of hygrometer measures the humidity directly in terms of mass flow rate and electric current and is therefore linear in humidity. Also, temperature has no influence on the moisture content. Although these features are desirable, it is considered that a simpler scheme using only one conductivity measurement is advantageous in a harsh environments. This is discussed later.

Moisture measurements are necessary for the control of many industrial processes where drying is involved. For example, control of drying in a paper mill requires a trouble-free, rugged sensor able to withstand moderate temperatures (<80° C.), atmospheres with organic vapors and dust and air speeds of the order of 10 m/s. Similar harsh environments occur in other industries. Many hygroscopic materials which have been used as sensing elements for hygrometers eventually become unreliable in operation because of surface contamination.

Polymers that adsorb water have been used as humidity sensors using a measurement of capacitance to infer moisture content. This type is made by Rotronic Instruments Corporation (ref. 2).

Pacer Systems offers a moisture sensor based on the adsorption of ultraviolet light by water vapor which is claimed to withstand 250° C. (ref. 3). Keeping the optical windows clean in dusty atmospheres may be difficult with sensors of this type.

Dew point hygrometers are based on thermoelectric cooling of a surface till dew settles on it. This condition is detected by a change of light reflection, capacitance (ref. 4) or attenuation of surface acoustic waves (ref. 5). Such sensors are not immune to surface contamination. In harsh environments, they perform very poorly.

The patent "Humidity Sensing and Measurement Employing Halogenated Organic Polymer Membranes," by Huang (ref. 6, U.S. Pat. No. 4,681,855) claims that a polymer like Nafion but with acid groups of both strong and weak acids (sulfonic acid and carboxylic acid in particular) has superior linearity and hysteresis properties. The claim of linearity is erroneous because Huang's supporting data clearly show that the conductance is a straight line in a logarithmic plot when plotted vs. relative humidity, which represents a power law. For example, this material changes its conductivity by a factor of 4000 when humidity changes from 30 to 100%!

Bare Nafion is much better because the relation between conductance and humidity is only a third degree curve over the whole range from 0 to 100%. This polymer Nafion is clearly usable over the whole range of humidities and not only upto 40% as erroneously claimed by Huang. The polymer containing two acid groups is inferior to bare Nafion as a humidity sensing element.

It turns out that lithium doped Nafion sensors are really linear over the range of humidities from 40% to 95%, in the range of temperatures of interest in paper drying application. Both Nafion and lithium-doped Nafion have excellent stability properties as well as negligible hysteresis. The present disclosure explains these in detail.

OBJECTS AND SUMMARY OF THE INVENTION

It is the primary object of the present invention to provide a system for obtaining the water vapor content or relative humidity of hot air in harsh industrial environments, in moving or quiescent air at moderate temperatures where many humidity sensors exhibit instability.

It is an object to produce a sensor which exhibits immunity to surface contamination in oily, dusty air streams containing organic vapors typical of those that occur in paper drying applications.

Temperatures in mill streams are typically near 65° C. and seldom exceed 80° C. The Nafion sensor is useful up to 175° C. It is an objective to measure both humidity and temperature by using small sensing elements so that accurate readings of the local environment are obtained. It is an objective to produce simple, compact sensors which are easy to clean and replace if need be.

The principle on which the sensor is based is the measurement of conductivity of a Nafion strip by using an alternating square wave current. Conditions of operation are designed to avoid polarization effects and sensor heating. The sensor unit also uses a current regulating device for temperature measurements. The electronic circuit and sensor head are designed to be very stable.

Tests in several paper mill streams have shown that the sensor has not changed its calibration after continuous exposure to the air stream for a period of more than one year! Materials used in the construction of this sensor such as glass, silver filled epoxy, platinum wire and Nafion contribute to its immunity to harsh environments. The sensor has low hysteresis, good time response and good sensitiveness for humidity control in paper manufacture. It may also be useful for the control of batch dryers in food and pharmaceutical industries.

BRIEF DESCRIPTION OF THE DRAWINGS

A more complete appreciation of the invention and the attendant advantage thereof will be more clearly understood by reference to the following drawings wherein.

DESCRIPTIONS OF THE PREFERRED EMBODIMENTS

I. Introduction

Figure 1:
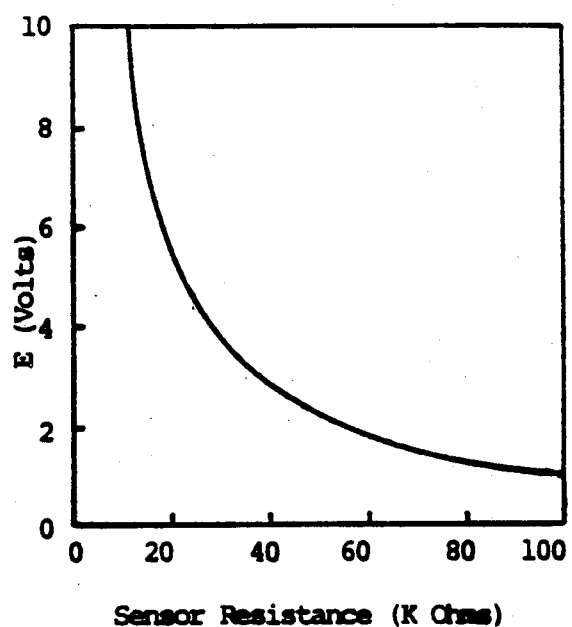
FIG. 1 is a plot of voltage output from the sensor which varies inversely as the resistivity of the sensor.

The accurate measurement and control of humidity may have been of little significance some fifty or sixty years ago when the subject was concerned mainly with meteorological practice. At the present time, it has very important implications in energy conservation and quality control of industrial processes.

The objective of this project was to investigate the feasibility of using a polymeric hygrometer for determining the relative humidity and the dry bulb temperature in harsh environments. The material chosen for use in the sensor is Nafion, which is a solid fluorocarbon polymer electrolyte that has a conductivity which varies as a function of relative humidity and temperature. Dupont's Nafion membrane was used in both H+ and Li+ ionic forms. The material "Nafion 117" is an unreinforced film of 1100 equivalent weight perflourinated copolymer. The maximum continuous operating temperature of Nafion is 175° C. in anhydrous systems and 220° C. in aqueous systems. The film thickness used was approximately 0.5 mm. A number of prototype sensor systems were fabricated and tested in the laboratory and in paper mills and the results are described.

II Principle of sensor operation

The key element of the sensor operation is DuPont's Nafion, a fluorocarbon polymer containing sulphonic acid. In the present application, Nafion is used under fairly dry conditions. In this case, water vapor is adsorbed on the surface. Experimental data demonstrating the characteristics of adsorption will be shown later. In the presence of the strong acid, water ionizes. Both H+ and OH− ions can transport charges. The conductivity of a strip of Nafion is measured by applying an alternating voltage to the strip and measuring the current through the strip. The conductivity measurement does not disturb the process of equilibrium between the water vapor outside and the surface phase of water on the Nafion strip because the ionic mobilities are much smaller than molecular velocities. Under the action of the alternating field, the ions move back and forth at very low drift speeds because the ion mobilities are very small. For example, H+ ions in solution move at a speed equal to $3.6 \times 10^{-3}$ cm/s. In the present case, mobilities of the ions on the surface may be of the same order of magnitude. If the electric field changes direction in 1 ms, the ions move only $3.6 \times 10^{-6}$ cm before reversing their direction.

We can now consider the process of adsorption of a gas, water vapor in this case, by a solid surface. The amount of gas adsorbed per unit mass of solid depends on the vapor pressure, temperature and on the nature of the gas and the solid. The adsorption isotherms are classified to be of five types. Calibration data show that the type II isotherm is observed in the present case. Water vapor adsorption by textile fibers is also of this type. The BET theory (Brunauer, Emmett and Teller) explains the various types of isotherms using the concept of fixed adsorption sites at which gas molecules settle on the surface to form adsorbed layers more than one molecule thick. The surface layers of the vapors outside are in dynamic equilibrium. The process of evaporation or condensation is associated with a heat of adsorption which is different for different layer thicknesses. The theory drives an equation for the adsorption isotherms using these concepts. The BET equation will be discussed later.

III. Calibration Procedures

The relation between voltage and the conductivity needs a calibration and the relation between the conductivity and the humidity needs another. The first calibration, which is for the electronics, is shown in FIG. 1, which is a plot of the electrical output of the Nafion hygrometer when a pure resistance is substituted for the Nafion element. The calibration is such that the output of the amplifier is proportional to the conductivity. The actual output voltage vs the sensor resistance is a rectangular hyperbola.

The electronic configuration of the hygrometer is basically that of a square wave driven AC Ohmmeter, which avoids electrochemical polarization effects.

Figure 2:
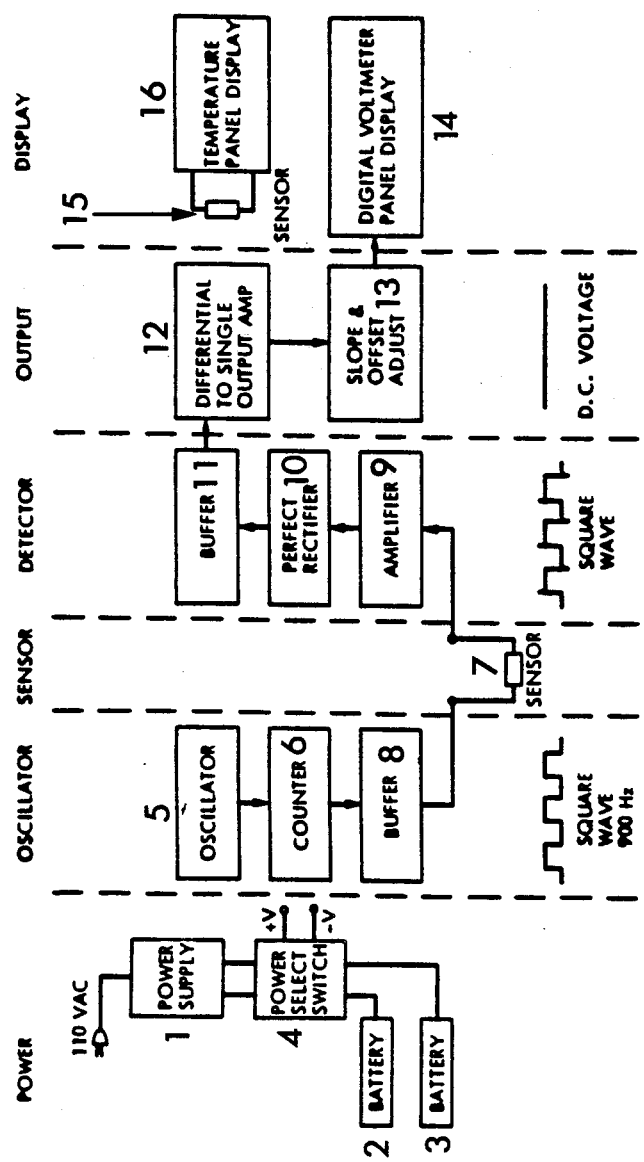
FIG. 2 is a sketch of the electronic block diagram which is essentially that of a square wave AC conductance meter reading in mhos together with an independent circuit for the measurement of temperature.

The measuring circuit is shown in FIG. 2. A power supply 1 energized by 110 V AC mains or batteries 2 and 3 supplies power to the instrument through a selector switch 4. A square wave current of frequency equal to 900 Hz generated by dividing down higher frequencies from the oscillator 5 by counter 6 is applied to the Nafion sensor 7 through a buffer amplifier 8. The voltage developed across the Nafion sensor 7 has spikes which are removed by suitable resistance-capacitance networks in amplifier 9, rectified perfectly by a perfect rectifier 10 and fed to a differential d.c. amplifier 12 through another buffer 11. Slopes and offsets are adjusted at amplifier 13 to get the output which is either a d.c. voltage in the range 0 to 1 V or 0 to 10 V or a d.c. current in the range 4 mamp to 20 mamp. A digital display 14 indicates the output d.c. voltage.

An independent circuit measures the temperature utilizing a current regulating device 15 which is the unit AD 590 available commercially. This solid state chip allows a current of 1 microampere to flow for 1° K. so that the current drawn by the chip indicates the temperature in a simple manner in the panel display 16. This is also available as a recorder output. The electronic circuit is enclosed in a sealed box approximately 20, 20, 25 cm and has selected components that will operate at the high temperatures and humidities encountered in the harsh mill environments. Surge and noise protection is also provided at the input.

The second calibration method uses standard solutions in small vials in which the Nafion sensor is calibrated by the use of the standard procedure ASTM E104 (1971). A small vial is partially filled with pure water for 100% relative humidity and with different salt or acid solutions that give lesser degree of water concentrations of the vapor phase in the vial. These salt solutions have limited humidity ranges obtainable by changes of temperature. Various concentrations of sulfuric acid in water allow calibrations over somewhat broader range of humidities at higher temperatures.

Figure 3:
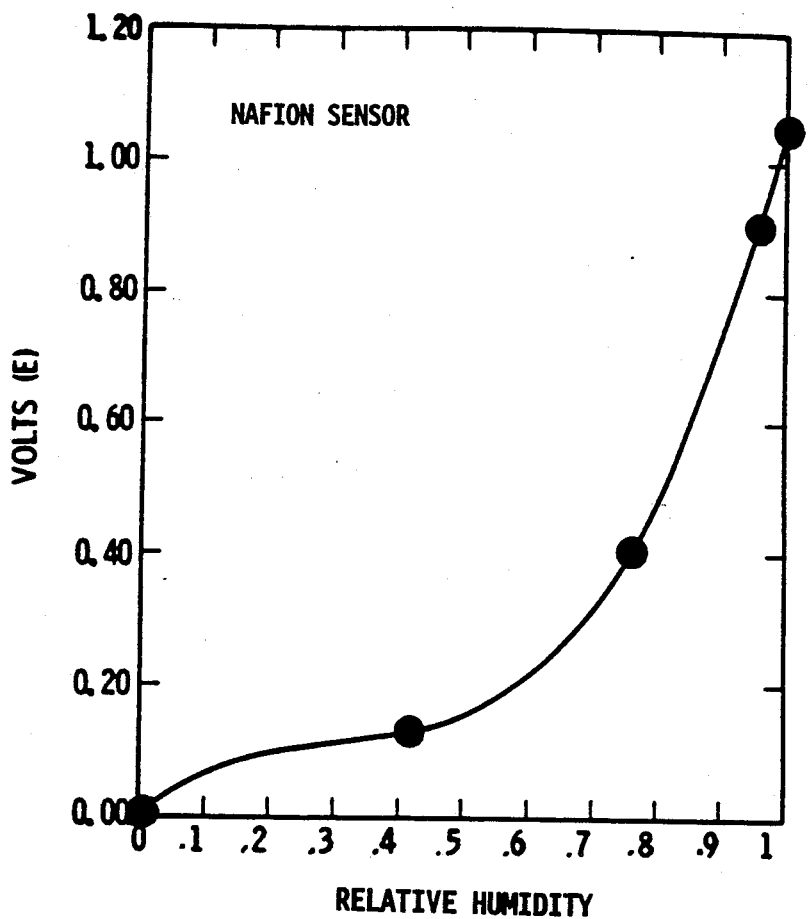
FIG. 3 is a calibration plot of a nafion strip at a temperature equal to 22.5° C.

In FIG. 3 is a plot of relative humidity (RH) vs Output Volts (E) of the hygrometer at 22.5° C. A cubic curve fits the data very well. The resultant equation for this is $$E = 0.84\,RH - 2.34\,RH^2 + 2.54\,RH^3. \tag{1}$$

Figure 4:
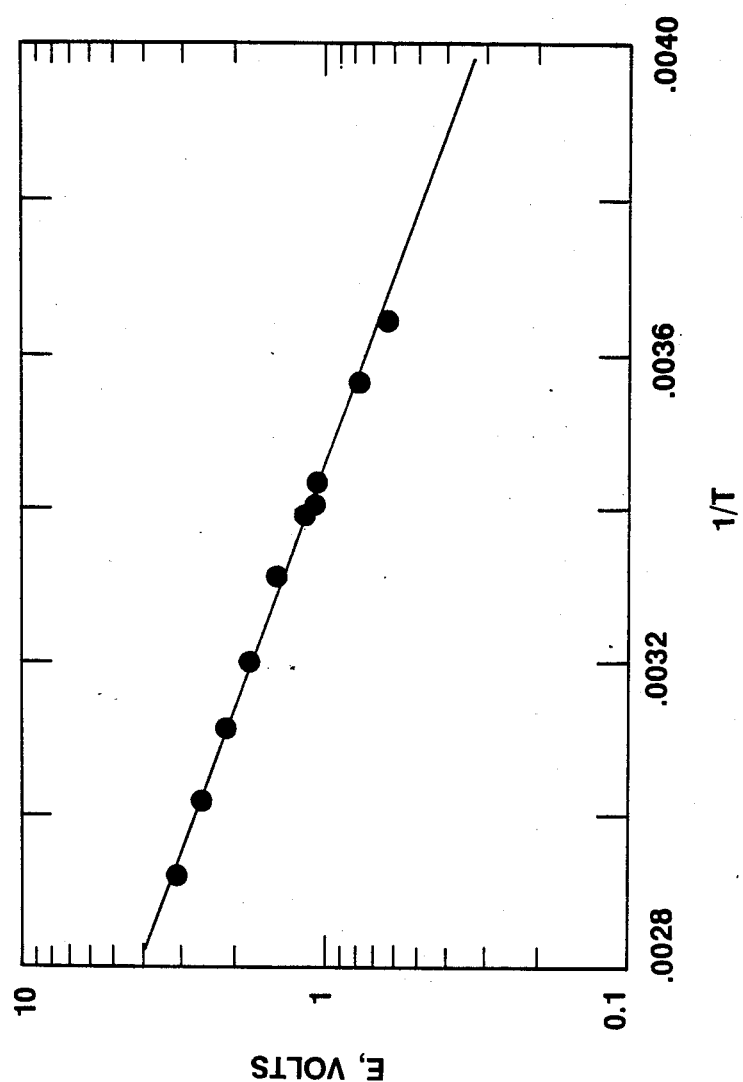
FIG. 4 is an Arrhenius type of plot of ln E versus 1/T, the data covering a temperature range 0° to 70° C.

FIG. 4 shows data obtained over water under saturation conditions over the range from 1.5° C. to 69° C. The nature of this line shows that the sensor element is measuring some function of the vapor pressure of water vapor which is itself a function of temperature. The slope of the Arrhenius line times the gas constant R is equal to the activation energy of sensor material with water vapor.

The proper fit to the data can be inferred from thermodynamics which suggests the structure of the equation relating E, RH and T. If a gas is in equilibrium with a liquid in which it is dissolved, the vapor pressure (P) of the gas and concentration (W) of dissolved gas are related by $$W = P\,\exp[B(T)/T], \tag{2}$$

where B(T) is the difference between the enthalpies in the two phases. If it is assumed that the conductivity is proportional to the concentration of water adsorbed by Nafion, the sensor output is $$E = P(T)\,\exp[B/T + A], \tag{3}$$

where P is in mm Hg, E is the output in volts and T is in °K. At a fixed temperature, E is seen to be not linear in RH or P (FIG. 3). This shows that either the solution model is not adequate or conductivity is not proportional to water absorbed by Nafion. The nature of the curve which starts with a small linear zone near RH=0, followed by a plateau and a sharp rise is characteristic of adsorption of gas molecules by surfaces. Initially gas molecules lie on the surface with low surface density, a monolayer forms, and as further mass accumulates, multilayers form. Adsorption of gases by solid surfaces is described by the well known BET theory which shows the following structure for the amount of gas adsorbed by unit mass of solid $$P/S\,(P_o - P) = 1/S_m C + (C-1)P/S_m C P_o \tag{4}$$

Here $S_m$ is the capacity of adsorption for a monolayer, C is a constant related to the heat of adsorption of the mono layer, P is the vapor pressure and $P_o$ is its saturation value. If we replace S, the actual coverage by the voltage E of the Nafion sensor, the above becomes $$RH/E\,(1 - RH) = 1/E_m C + (C-1)RH/E_m C. \tag{5}$$

Figure 5:
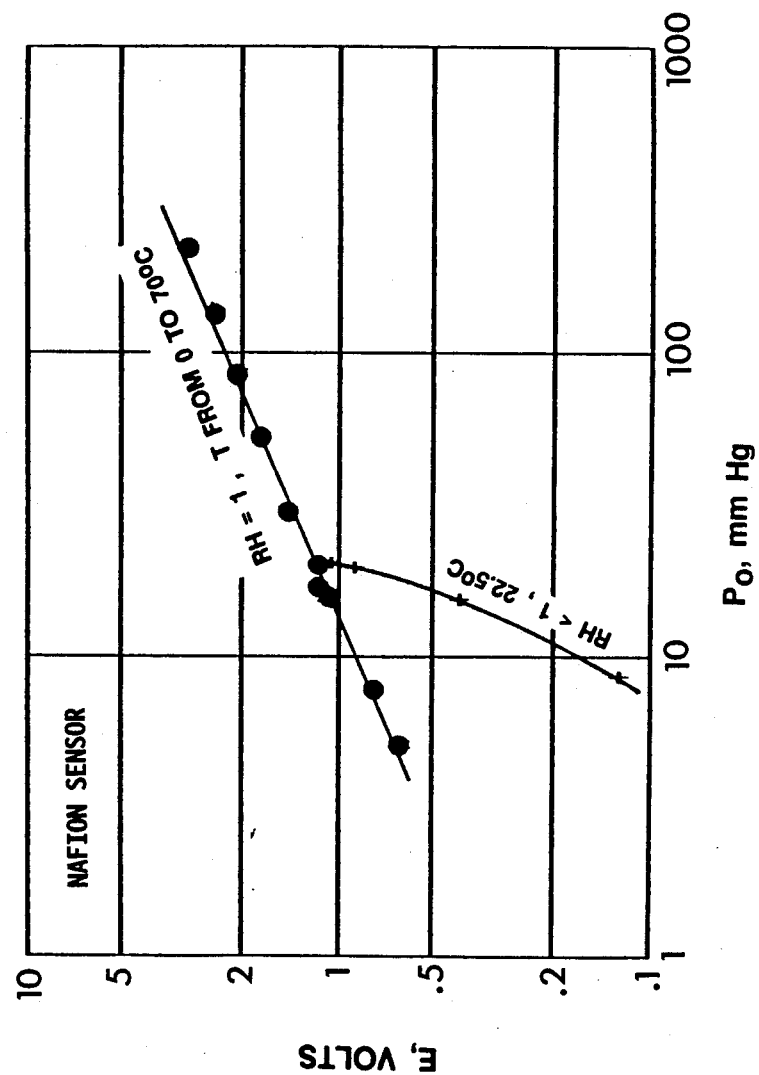
FIG. 5 is a plot of the sensor output plotted versus the vapor pressure of water under saturation conditions from 1.5° to 69° C. and at unsaturated conditions at a fixed temperature equal to 22.5° C.

The BET plot of $RH/E(1-RH)$ vs RH is a straight line typically in the region upto 1.5 monolayers thick. The plot is found to be straight from RH=0.1 to RH=0.8. A plot of E vs $P_o$ is shown in FIG. 5 using the data obtained at temperatures from 1.5° to 69° C. over pure water. The equation satisfying this data (dark circles) is $$E = 0.327\,P_o^{0.423} \tag{6}$$

In the same figure, data obtained at 22.5° C. over solutions of sulfuric acid, are seen to lie on a different curve with much higher slope. The simple rule that E is proportional to P is not observed. The nature of the curve in FIG. 3 suggests that the phenomenon of adsorption on the surface (both inside and outside the pores) of Nafion is involved.

Relative Humidity

Figure 6:
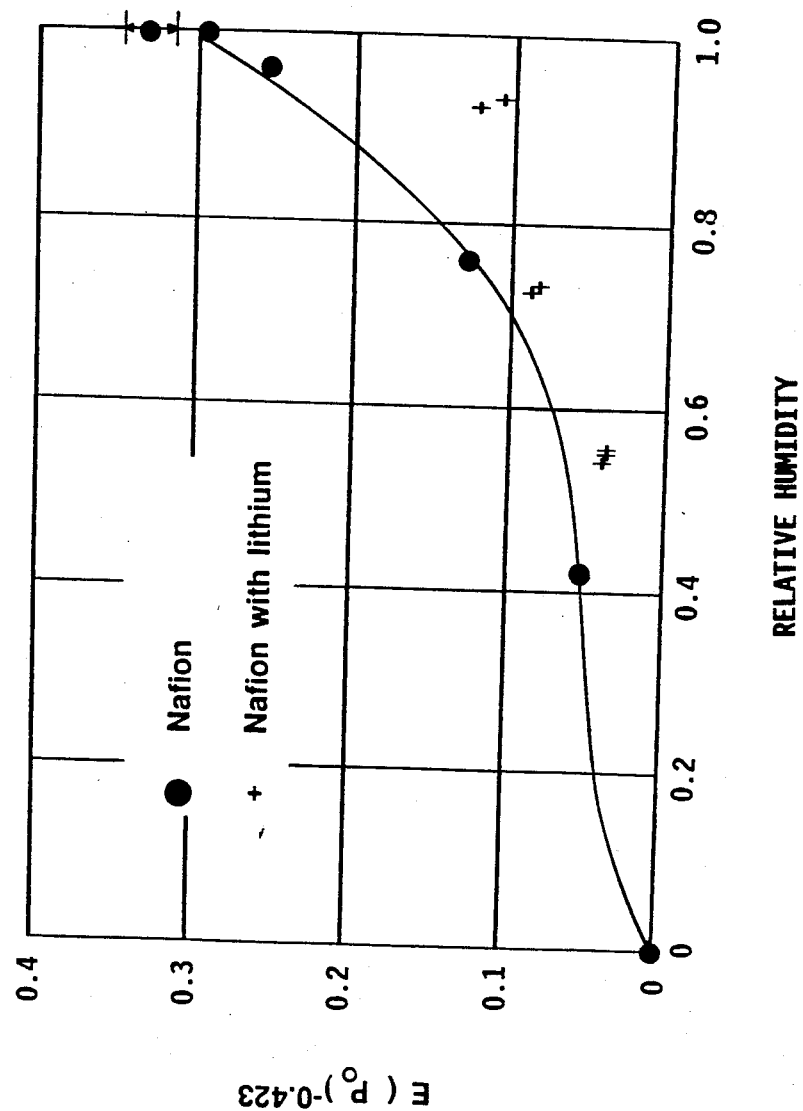
FIG. 6 is a normalized plot of $E/p_o^{0.423}$ vs relative humidity RH which correlates both data obtained at R < 1 and at RH = 1 shown as dark circles, with the corresponding data for Nafion containing lithium shown as plusses.

Adsorption phenomena are characterized by a strong dependence on the relative humidity of the environment. In general, a law of the form $$E = 0.327\,P_o^{0.423} f(RH) \tag{7}$$

could be useful for correlating data. A plot of $E/P_o^{0.423}$ vs RH is shown in FIG. 6 where $$f(RH) = 0.35\,RH - 0.89\,RH^2 + 0.85\,RH^3. \tag{8}$$

Data obtained at RH=1 at different temperatures are shown as a dark circles with the extent of variation of the ordinate indicated by the arrows and bars. The other points lie on the 22.5° C. isotherm.

Figure 7:
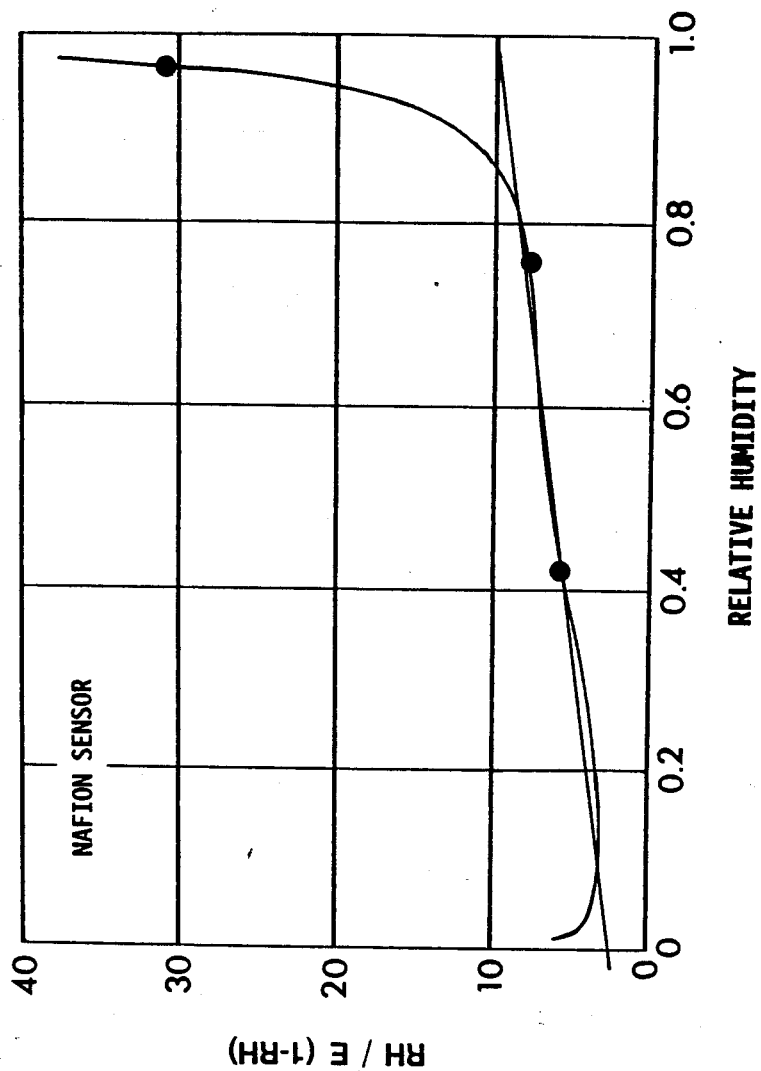
FIG. 7 shows a BET plot showing the existence of a linear zone with RH extending upto RH = 0.8 characteristic of an adsorbed monolayer of water.

In FIG. 7, the BET plot is shown where $RH/E(1-RH)$ is plotted against RH. Equation (1) and the actual data points excluding RH=0 and RH=1 are also shown. It is clear that from RH=0 to 0.8, the linear zone is observed indicating that surface accumulation is not more than 1.5 monolayers thick. This region of RH is normally encountered industrially in drying processes.

Tests on a modified sensor

It was felt that treating Nafion with lithium hydroxide to introduce Li ions into the material would have the beneficial effect of making the Nafion less prone to contamination by organic vapors. This treatment decreases the conductivity, however, to approximately one half the original value. A comparison of the calibration of the original sensor with the modified is done by plotting the same quantities in FIG. 6. These data points are shown as plusses. Data were obtained for relative humidities in the range 0.5 to 1 using sulfuric acid of various concentrations. The data is not dense enough to identify the type of adsorption isotherm but it appears to be of type V. All the data points do not belong to the same temperature, and it has been assumed that $E/P_0^{0.423}$ accounts for the temperature variations as in the case of untreated Nafion. The field tests at a linear board plant involved expected temperatures of 50° to 65° C. with relative humidities of above 50%. In this parameter envelope the calibration data appear to be linear with fixed slopes. The approach used was a multiple linear regression analysis for two independent variables. This take the form $$RH = a + bT + cE, \quad (9)$$

where T is in ° C. and E is in volts.

Figure 8:
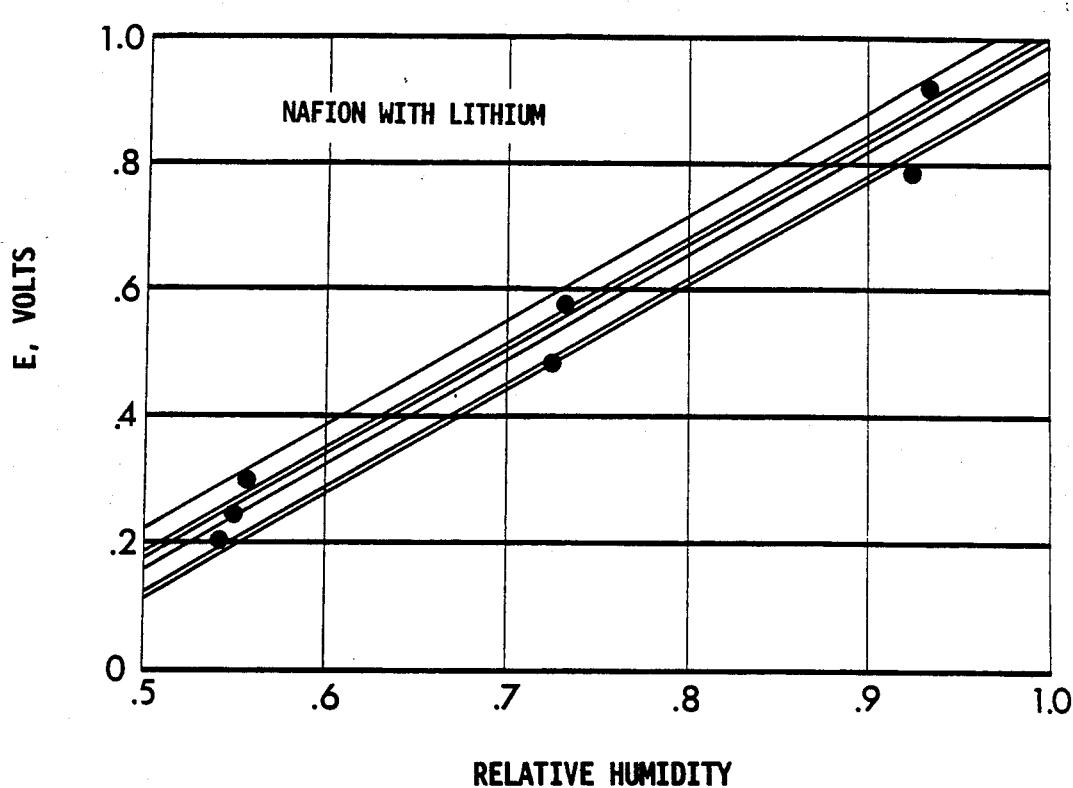
FIG. 8 shows a calibration of a sensor containing lithium at temperatures equal to 47.2, 49.4, 57.8, 61.1 and 71.1 going from bottom to top together with data points and straight line fits, the data being obtained by locating the sensor in sealed vials over acid solutions of different strengths.

The data points and the straight lines drawn at the same temperatures at which the data were obtained are shown in the FIG. 8. The six straight lines are for temperatures equal to 47.2°, 49.4°, 57.8°, 61.1°, 63.3° and 71.1° C., going from bottom to top. Of the seven data points, two are at the same temperature (49.4° C.) with different values of RH. In FIG. 8 the results are given from the data obtained by using Nafion sensor element of size 0.88×10 mm. The straight line plots in FIG. 8 correspond to the equation $$RH = 0.57 - 0.0028\ T + 0.61\ E \quad (10)$$

Trials of the Nafion Hygrometer containing Lithium ions

Figure 9:
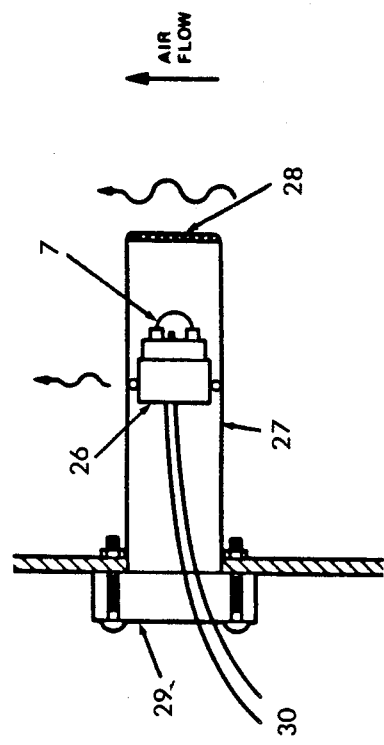
FIG. 9 shows a sketch of a typical mounting of the sensor in an air duct.

The sensor element was placed in the paper machine dryer exhaust hood system. The impacting air on the sensor had a velocity of about 10 m/s (2000 ft/min) and a temperature range of 45° to 60° C. (110° to 140° F.). The expected relative humidity was from 0.5 to 0.9. The sensor device was protected from the direct air flow as shown in FIG. 9, by using a shielding tube 27 with porous ends of nickel wire 28 at the end to prevent direct impingement of high velocity air on the sensor. Flange 29 is used to mount the tubular shield 27 and the signals are led out by a multicore cable 30.

Figure 10:
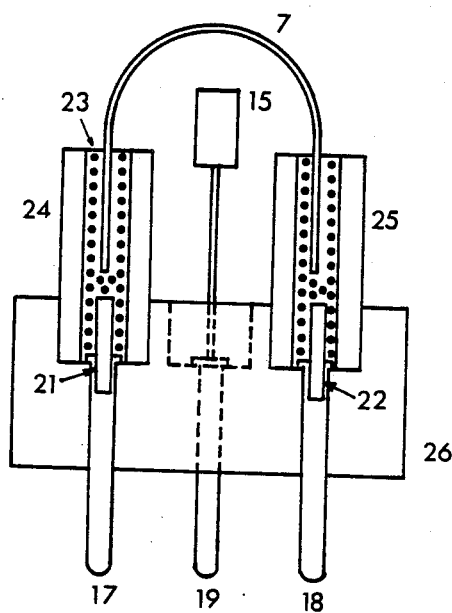
FIG. 10 shows the method of construction of the sensor where contacts are established by silver filled epoxy.

The hygrometer configuration is shown in two cross sectional views in FIG. 10. A Teflon base 26 of diameter 1 inch, contains four gold coated contact pins of which 17 and 18 connect to a Nafion strip 7 through platinum wires 21 and 22 and silver filled epoxy 23 filling the capillary bores of glass capillaries 24 and 25. Pins 19 and 20 similarly connect to the temperature sensor 15 in the cross section at right angles to the plane of the Nafion strip 7. The four pin base connects to a 4 wire shielded cable for connection to the measuring circuit shown earlier in FIG. 2. A suitable size for the Nafion strip can be 10 mm.×2 mm.×0.2 mm.

V. Sensor applications

Apart from the measuring of humidity in a harsh environment, the Nafion hygrometer can be used as a process control element in applications such as:
a. Process control of batch and continuous type dryers in the food and pharmaceutical industry,
b. Heat recovery systems involving humid air as in dryers and air conditioning systems.

In most such applications an accurate knowledge of the wet bulb temperature of a moving air stream is required. Measurement of the wet bulb temperature is the most difficult to perform in hot air streams and within dryers since the conditions are such as to promote rapid evaporation. The measurement of the dry bulb temperature and the relative humidity by the present sensor provides a method of estimating, with the help of a psychrometric chart, the wet bulb temperature accurately. To be used as a control element, the sensor needs to be characterized properly by specifying its sensitivity (the output of sensor in volts per a unit change in relative humidity at a constant temperature) and its time constant. In the following we discuss these issues as well as consider applications which demonstrate the possible uses for the Nafion hygrometer.

Psychrometry

In order to understand and appreciate the discussions to follow we present here, some basic concepts from psychrometry, the study of moist air. A psychrometric chart describes completely the state of moist air. At a given total pressure (say the atmospheric pressure 101.32 KPa) any two of the following quantities completely describe the state of moist air:
a. Dry bulb temperature (°C.)
b. Wet bulb temperature (°C.)
c. Absolute humidity (Kg water per Kg dry air)
d. Relative humidity (partial pressure of water vapor/partial pressure of water vapor at saturation)
e. Specific volume ($M^3$/Kg dry air)

The Nafion hygrometer represents the psychrometric chart within the useful range of the instrument since it measures the dry bulb temperature and the RH simultaneously.

Nafion hygrometer as control element

In order that the sensor be useful as a control element the following must be known:
a. The response time of the sensor
b. The sensitivity of the sensor and the dependable and repeatable operation within the range of the variables encountered in practice.

Figure 11:
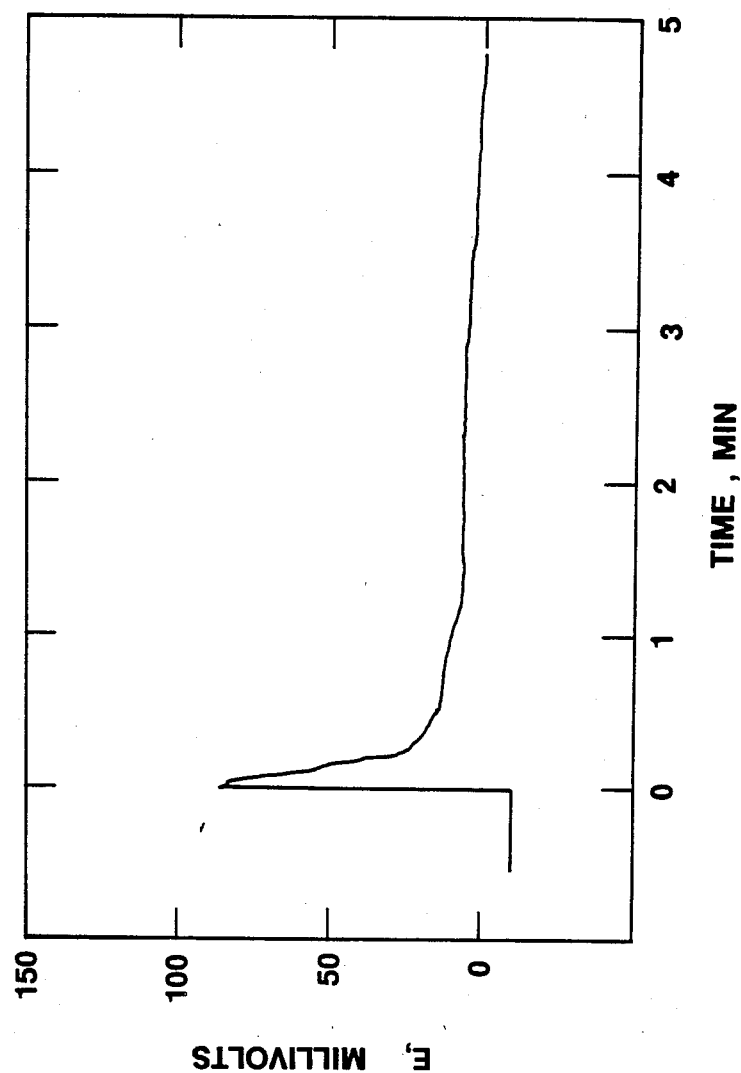
FIG. 11 shows the response of a Nafion hygrometer to a whiff of moist air blown across it in still air.
Figure 12:
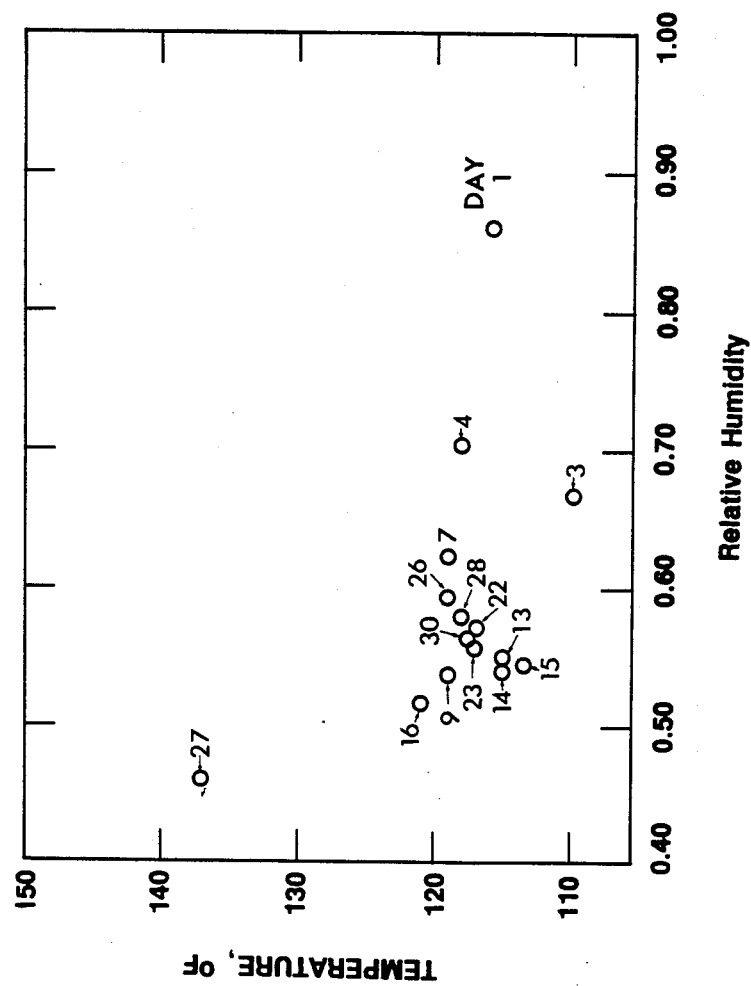
FIG. 12 is a plot of temperature and relative humidity conditions encountered in a paper mill duct, the data being read daily, showing that normally the mill stream operates near 115° F. and RH = 0.55.
Figure 13:
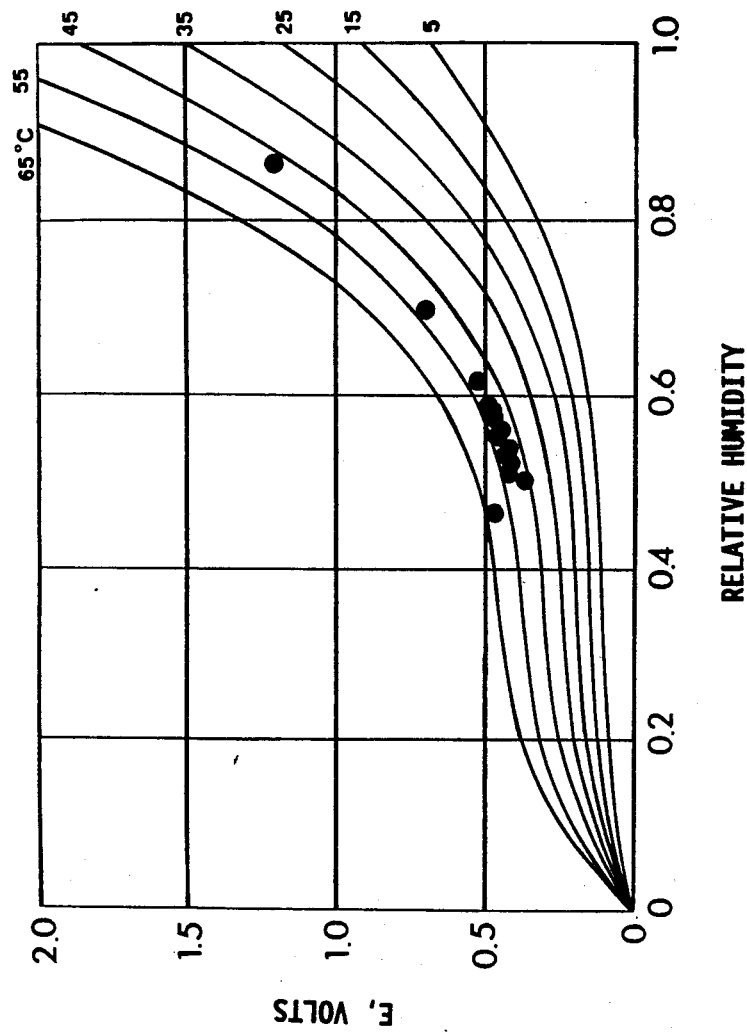
FIG. 13 is a comparison of E vs. RH data with the theoretical characteristics of Nafion over the range of values encountered in the mill air duct showing that the sensor output is a sensitive indicator of RH.

These characteristics are considered now as applicable to the Nafion sensor.
a. Response time of the sensor:
From the application point of view the sensor should have a response time much smaller than the response time of the system which is to be controlled. In the case of paper mill applications the system time constant of approximately 10 minutes is primarily due to heat transfer rate limitations in the mill. The Nafion sensor has a response time typically like 15 seconds as can be seen from FIG. 11. This figure shows the response of the sensor to a whiff of moist air blown across it when the sensor was in front of a miniature fan of 3 cm diameter. This clearly shows that the Nafion sensor has excellent time response characteristics.
b. Sensitivity of the sensor to changes in the mill environment:
Several mill trials were conducted to gather data to demonstrate their suitability for operation with the temperature and humidity variations that take place in such applications. The data from a mill has been converted to the dry bulb temperature - relative humidity data plotted as FIG. 12. The data show that the range of the variables over a month of operation was: a. RH—0.46 to 0.86, b. dry bulb temperature —43° to 58° C. (110° to 137° F.). This range is well within the conditions used for calibrating the sensor in the laboratory. FIG. 12 clearly demonstrates that the sensor sensitivity is adequate to delineate RH differences of ½% or so. The data also shows that the mill was operating, for the most part, in a narrow region between 43°–48° C. (110°–120° F.) and 0.5–0.6 RH. FIG. 13 shows the data plotted on the isotherms of the bare Nafion hygrometer to demonstrate the fact that the hygrometer meets with the range and sensitivity requirements in plant operations. The hygrometer has also operated in the harsh mill environment for several months without any degradation in performance. Given these it is clear that the Nafion hygrometer can be used for process control applications.

Other Benefits

Figure 14:
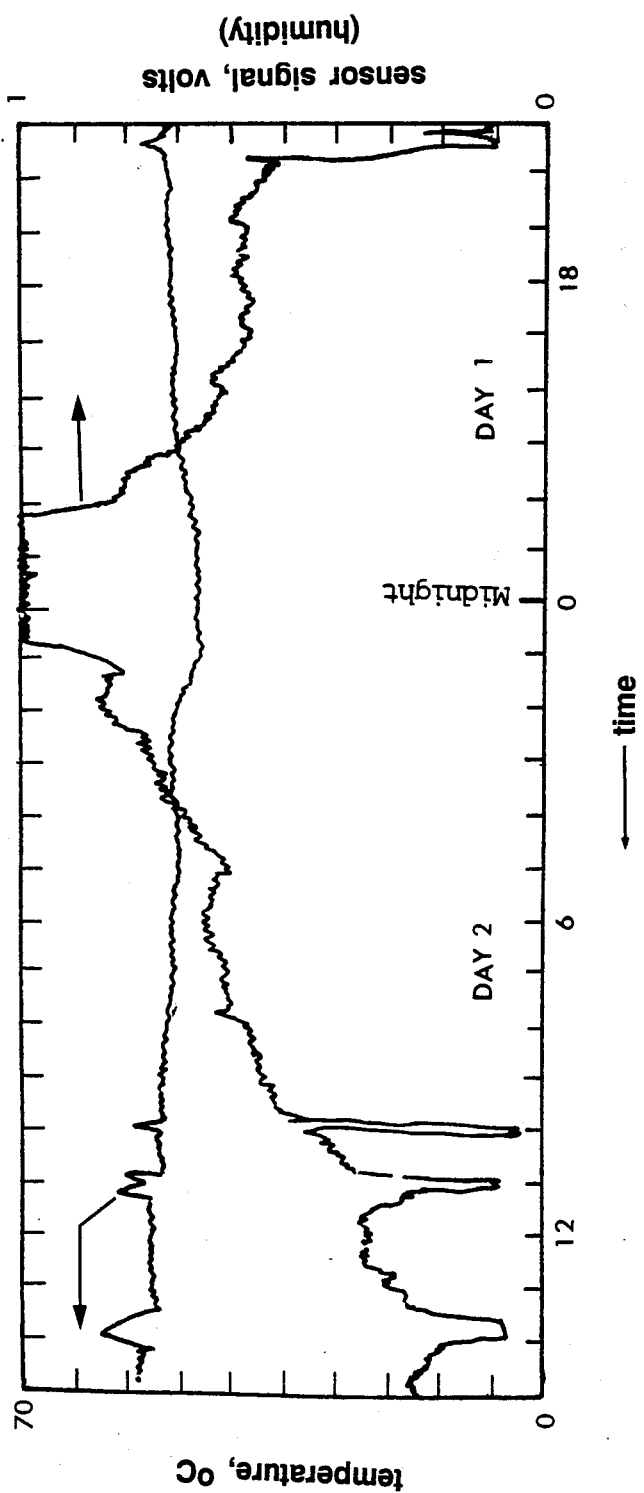
FIG. 14 is a piece of continuous data where the humidity signal varies substantially more than the temperature; spikes at paper breaks are larger in the humidity signal and breaks tend to occur more frequently when the humidity is low; all of which indicate the usefulness of the humidity sensor for control of the mill air stream.

It is observed that the temperature and humidity in the duct vary cyclically. When the temperature is high, the humidity goes down and vice versa. A sample of data obtained at the mill illustrates this point. In FIG. 14 recorder traces of signals from a Nafion sensor with Li are shown. Each division on the time axis corresponds to 1 hour and the time runs from right to left. The humidity signal range is 0 to 1 volt.

Whenever there is a paper break, the humidity signal decreases and the temperature signal increases. After such a break, signals take appoximately an hour to reach their normal values. The temperature range on the chart is 0° to 70° C. so that each division represents 7° C.

The E signals go beyond 1 volt after rising rather suddenly in day one. It is possible that moisture condensed on it. At the same time, the temperature trace shows a decrease.

Paper breaks seen to occur more frequently when RH is low. In these case T is higher than normal and it is possible that the paper is too dry. If this is true in general, controlling the duct humidity to a higher value could reduce the number of paper breaks, which would be very beneficial, of course. In addition, maintaining higher humidity saves energy. Temperature changes are much smaller than humidity voltage changes and it would appear that the humidity signal would be better for control purposes.

VI. Conclusions

The lithium-doped Nafion hygrometer is an attractive sensor for the paper and pulp industry. Materials used in the design such as glass, silver filled epoxy, platinum wire and Nafion exhibit immunity to the harsh environments containing organic vapors and dust. The sensor has low hysteresis, good time response and sensitiveness for humidity control in paper manufacture. It may be useful for the control of bath dryers in food and pharmaceutical industries also.

The embodiments of the invention in which an exclusive property or privilege is claimed as defined as follows:

1. A sensor for deriving data incidative of relative humidity and temperature of air in drier ducts, ovens and so forth comprising a lithium-doped Nafion strip mounted across two glass capillaries embedded in a Teflon base, with the ends of said Nafion strip embedded in a filling of conducting silver-filled epoxy; said filling also providing electrical connections to a pair of gold coated brass pins through platinum wires also embedded in said filling; a temperature sensor mounted across another pair of pins located on said base on a line at right angles to a line joining said first pair of pins; multi conductor cables which connect said sensors to two measuring circuits; one of said circuits comprising means for power, square wave generation, buffered amplification, inversion, perfect rectification and means for amplified output, which produces an output voltage or current proportional to the conductance of said Nafion sensor; the other said measuring circuit producing an output proportional to temperature of said temperature sensor; a tubular shield with porous ends in which said sensor is housed to prevent excessively high speeds air from blowing directly on said sensor; output means for displaying outputs from said measuring circuits, calculating relative humidity and temperature and generating useful control signals to utilize said calculated relative humidity and said calculated temperature of air in said duct or oven.

2. A sensor as described in claim 1 wherein said Nafion strip exposed to the atmosphere is of size approximately equal to 10 mm×2 mm×0.2 mm.

3. A sensor as described in claim 1 wherein said Nafion strip is treated with lithium hydroxide to introduce lithium ions into its structure so as to produce greater resistance to contamination by organic vapors in the environment.

4. A sensor as described in claim 1 wherein said one measuring circuit utilizes square waves of approximately 900 Hz to measure the conductivity of said Nafion sensor free of electric polarization effects.

* * * * *